US00PP35706P2

(12) United States Plant Patent
Ployphommas

(10) Patent No.: US PP35,706 P2
(45) Date of Patent: Mar. 26, 2024

(54) ***MONSTERA* PLANT NAMED 'SUMI1'**

(50) Latin Name: *Monstera deliciosa*
Varietal Denomination: Sumi1

(71) Applicant: Paiboon Ployphommas, Nong Sam Wang (TH)

(72) Inventor: Paiboon Ployphommas, Nong Sam Wang (TH)

( * ) Notice: Subject to any disclaimer, the term of this patent is extended or adjusted under 35 U.S.C. 154(b) by 0 days.

(21) Appl. No.: 18/445,183

(22) Filed: May 15, 2023

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Zachariah Allan Kay
(74) *Attorney, Agent, or Firm* — Samuel R. McCoy, Jr.

(57) ABSTRACT

'Sumi1' is a new and distinctive *Monstera* plant which is characterized by a small stature, relatively small laminas borne on short petioles, glossy dark green foliage that is flecked and blotched with cream white, and the stability of all characteristics from generation to generation. The new variety is typically produced as an indoor ornamental plant.

2 Drawing Sheets

Latin name of the genus and species: The Latin name of the genus and species of the novel variety disclosed herein is *Monstera deliciosa.*

Variety denomination: The inventive variety of *Monstera* disclosed herein has been given the variety denomination 'Sumi1'.

BACKGROUND OF THE INVENTION

Parentage: The claimed plant originated as an induced, whole-plant mutation of *Monstera deliciosa* 'Thai Constellation' at a plant tissue culture laboratory in Nong Sam Wang, a subdistrict in the Nong Suea district of Pathum Thani province, Thailand. First the inventor harvested explants from a 'Thai Constellation' (not patented) plant at his commercial plant tissue culture laboratory. These 'Thai Constellation' explants were then cultured with a combination of 1.0 mg/L of benzyl adenine (BA) and 0.1 mg/L of 2,4-dichlorophenoxyacetic acid (2,4-D) to induce both callusing and mutation. Once the cultures were callused, they were treated with 1.0 mg/L benzyl adenine (BA) to induce foliar shoot development and growth. In February of 2019, once foliage had developed, the inventor observed one cultured plantlet that exhibited a smaller stature than the parent. Said culture was deflasked, acclimatized, and grown to a mature size in order to confirm the distinctness and stability of the characteristics first observed. After further evaluation, it was determined that the smaller stature of the claimed plant would prove favorable for commercial marketability.

Asexual Reproduction: Asexual reproduction of 'Sumi1', by way of leaf cuttings, was first performed in March of 2019 at the inventor's greenhouse in Nong Sam Wang, a subdistrict in the Nong Suea district of Pathum Thani province, Thailand. 'Sumi1' was subsequently reproduced by way of meristematic tissue culture propagation in February of 2020. Five successive generations so produced have shown that the unique features of the instant cultivar are stable and reproduced true to type.

SUMMARY OF THE INVENTION

The cultivar 'Sumi1' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Monstera* cultivar 'Sumi1'. These traits, in combination, distinguish 'Sumi1' as a new and distinct cultivar.

1. *Monstera* 'Sumi1' exhibits a compact growth habit and a small stature; and
2. *Monstera* 'Sumi1' exhibits relatively small laminas which are moderately incised and fenestrate; and
3. *Monstera* 'Sumi1' exhibits short petioles; and
4. *Monstera* 'Sumi1' exhibits dark green to yellow-green foliage that is irregularly blotched and flecked with a mixture of white, yellow-white, and orange-white; and
5. *Monstera* 'Sumi1' exhibits sporadic blistering of the epidermis in the form of irregularly shaped, translucent-white blotches.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
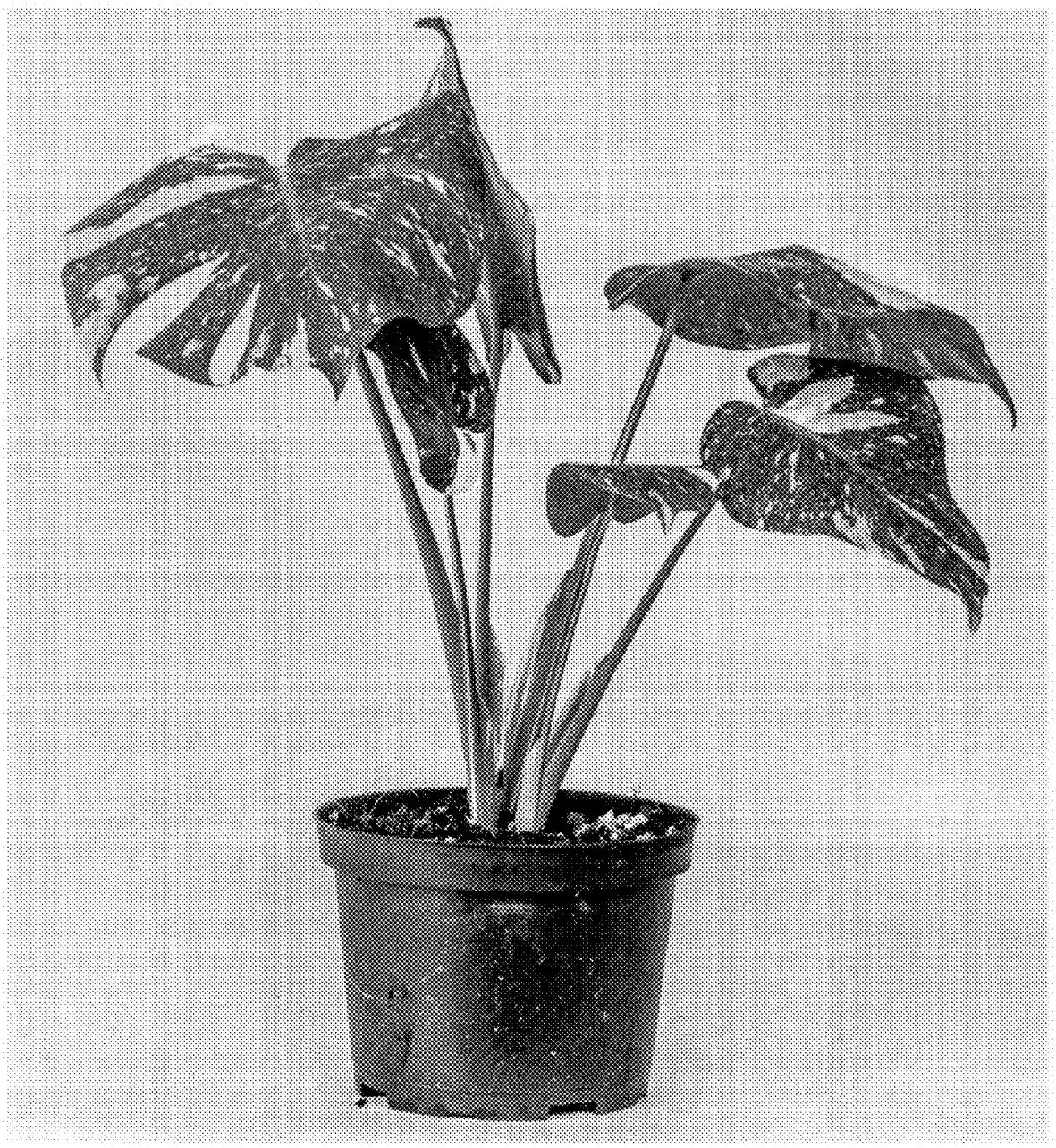
FIG. 1 shows, as nearly true as it is reasonably possible to make the same in color illustrations of this type, an exemplary plant of the new cultivar, 'Sumi1'. The plant shown is approximately 12 months old from a rooted cutting, potted into a 15 cm nursery container, grown in a greenhouse in Nong Sam Wang, a subdistrict in the Nong Suea district of Pathum Thani province, Thailand.
Figure 2:
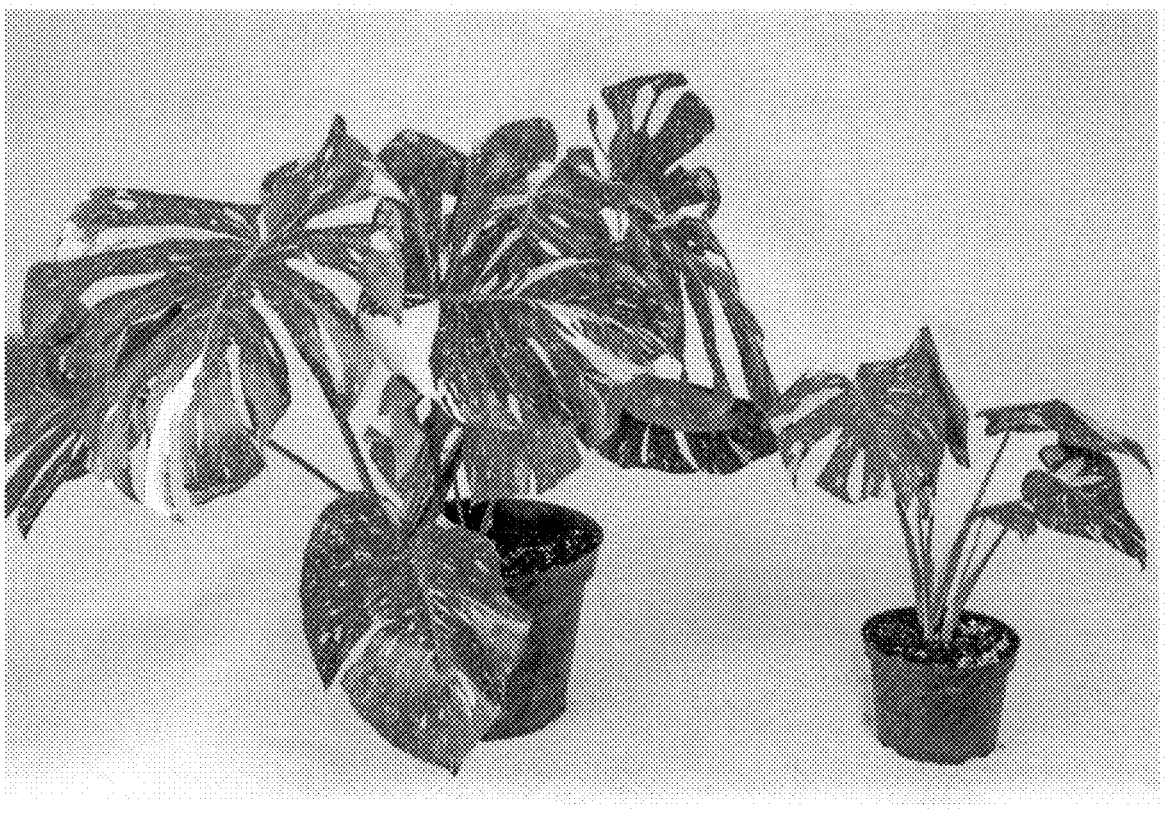
FIG. 2 shows the difference in size between a 12-month-old 'Thai Constellation' plant (on the left) and a 12-month-old 'Sumi1' plant (on the right).

With the exception of the stem description, the following observations and measurements made in April of 2023 describe a 12-month-old 'Sumi1' plant grown in a 15 cm nursery container at commercial greenhouse in Nong Sam Wang, a subdistrict in the Nong Suea district of Pathum Thani province, Thailand. A 3-year-old 'Sumi1' plant, grown in a 25 cm container, at the same location and in the same manner as the 12-month-old plants, was used for the stem description. Plants were produced using conventional greenhouse production protocols for *Monstera* which consisted of growing under 70-percent shade cloth, regular overhead irrigation every two days, and slow-release granular fertilizer applications at 4-month intervals, approximately. Preventative applications of Imadacloprid and Metalyx pesticides were utilized to prevent insect infestations and fungal infections. No photoperiodic treatments or artificial light was given to the plants.

Those skilled in the art will appreciate that certain characteristics will vary with older or, conversely, with younger plants. 'Sumi1' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on The Royal Horticultural Society Colour Chart, The Royal Horticultural Society, London, 1986 (second edition).

A botanical description of 'Sumi1' and comparisons with the parent and the most similar variety of common knowledge are provided below.

General plant description:

*Growth habit.*—Monopodial evergreen perennial; plants will eventually develop a stem with age.

*Plant profile.*—Upright, globular.

*Height.*—27 cm.

*Width.*—37 cm.

*Plant vigor.*—Moderately vigorous.

*Propagation.*—Method — Meristematic tissue culture. Time to initiate roots — Approximately 8 weeks to initiate roots at approximately 25 degrees Centigrade. Crop time — Approximately 24 to 30 weeks to produce a well-rooted, marketable 15 cm container from a rooted cutting.

*Environmental tolerances.*—Moderately high tolerance to rain; low to moderate tolerance to wind; not drought tolerant; tolerant of temperatures to at least 35 degrees Celsius. Cold hardy to USDA Hardiness Zone 10.

*Pest resistance and susceptibility.*—Plants have not been observed to be any more or less susceptible or resistant to pathogens and pests common to *Monstera* sp.

Root system:

*General.*—*Monstera* sp. has the propensity to produce both subterranean and aerial roots, though only subterranean roots have been observed on the claimed plant.

*Branching.*—Freely branched.

*Density.*—Moderately dense.

*Distribution.*—Subterranean roots are shallow to moderately deep.

*Texture.*—Fleshy; smooth; lacking root hairs.

*Color.*—Yellow-white, nearest to a mixture of RHS 158A and 158B.

Stems:

*Branching characteristics.*—*Monstera* sp. is a monopodial plant; plants eventually develop a stem with age.

*Aspect.*—Rounded.

*Length.*—Approximately 5.5 cm.

*Width.*—Approximately 2.0 cm.

*Internode length.*—Approximately 1.0 cm.

*Strength.*—Moderately strong.

*Texture.*—Glabrous.

*Luster.*—Matte to very slightly glossy.

*Color, adaxial surface.*—Green, nearest to in between RHS 139B and 141B, and occasionally streaked with a mixture of yellow-white, nearest to RHS 158C, and yellow, nearest to RHS 5D.

Foliage:

*Arrangement.*—Alternate to spiraled.

*Division.*—Simple.

*Attachment.*—Petiolate.

*Quantity of leaves per shoot.*—1.

*Quantity of shoots per plant.*—6.

*Quantity of leaves per plant.*—6.

*Lamina.*—Shape — Broadly cordate to broadly ovate; laminas become progressively pinnatifid and perforated with age. Apex — Broadly acuminate. Base — Cordate. Aspect — Convex. Attitude — Outward to somewhat pendulous, at an approximate angle of 90 degrees to the petiole. Dimensions — 17.8 cm long and 22.9 cm wide. Margin — Juvenile foliar margins are entire with light, coarse undulation. Mature foliar margins are incised, lobed, and fenestrated. Texture and luster, adaxial surface — Sporadic blistering of the epidermis is present in the form of irregularly shaped, translucent-white blotches. Otherwise, the laminar surface is smooth, glabrous, and glossy. Texture and luster, abaxial surface — Smooth, glabrous, and slightly glossy to matte. Juvenile color, adaxial surface — Nearest to a mixture of green and yellow-green; RHS 139A, 141A, 141B, 143A, 143B, and 144B, yet nearest to RHS 141A; irregularly flecked and blotched with a mixture of white, RHS 155A, and yellow-white, nearest to RHS 158C. Additionally, the areas of the laminar surface with epidermal blistering appear as translucent-white blotches, nearest to RHS 155A, revealing the flecks and blotches beneath. Juvenile color, abaxial surface — Nearest to a mixture of green and yellow-green; RHS 143C and 144B, yet nearest to RHS 144B; irregularly flecked and blotched with a mixture of white, RHS 155A, and yellow-white, nearest to RHS 158C. Mature color, adaxial surface — Nearest to a mixture of green and yellow-green, RHS 141B, 143A, 143B, and 144B, yet nearest to RHS 144B; irregularly flecked and blotched with a mixture of white, RHS 155A, and yellow-white, nearest to RHS 158C, and orange-white, nearest to in between RHS 159C and 159D. Additionally, the areas of the laminar surface with epidermal blistering appear as translucent-white blotches, nearest to RHS 155A, revealing the flecks and blotches beneath. Mature color, abaxial surface — Yellow-green, nearest to in between RHS 144C and 145A; irregularly flecked and blotched with a mixture of white, RHS 155A, and yellow-white, nearest to RHS 158C, and orange-white, nearest to in between RHS 159C and 159D. Venation — Vein pattern — Pinnate. Vein color, adaxial surface — The main vein and largest lateral veins are nearest to in between green, RHS 143C, and yellow-green, RHS 144A; all other lateral veins are indistinguishable from the surrounding laminar surface. Vein color, abaxial surface — The main vein and largest lateral veins are yellow-green, nearest to in between RHS 145A and 145B; all other lateral veins appear as a dark shade of green as a result of light penetration through the lamina, nearest to RHS 139A.

*Petiole.*—Attachment — Sheathed. Aspect — Rounded. Length — Approximately 25.4 cm. Width — Approximately 3.8 cm, including the petiole wings, at the proximal end and 1.25 cm at the distal end. Strength — Moderately strong. Texture — Verrucose; glabrous. Luster — Matte to very slightly glossy. Color, adaxial surface — Juvenile petioles are nearest to in between green, RHS 143C, and yellow-green, RHS 144A; mature petioles are yellow-green, nearest to RHS 145A, and occasionally longitudinally striped colored with a mixture of white, RHS 155A, and yellow-white, nearest to RHS 158C. Color, abaxial surface — Juvenile and mature petioles are yellow-green, RHS 145B, and occasionally longitudinally striped colored with a mixture of white, RHS 155A, and yellow-white, nearest to RHS 158C. Geniculum — Length — 2.5 cm. Diameter — 0.95 cm. Texture and luster — Matte to very slightly glossy. Color, adaxial surface — Juvenile petioles are nearest to in between green, RHS 143C, and yellow-green, RHS 144A; mature petioles are yellow-green, nearest to RHS 145A. Color, abaxial surface — Juvenile and mature petioles are yellow-green, RHS 145B. Petiole wings — General Description — Two petiole wings are present at the base of each petiole. Length — Approximately 7.6 cm. Width — Approximately 1.25 cm at the base. Margins — Entire; involute; lightly undulated. Texture and luster — Glabrous and very slightly glossy. Color, adaxial surface — Yellow-green, nearest to in between RHS 143A and 143B, with irregular longitudinal stripes colored with a mixture of white, RHS 155A, and yellow-white, nearest to RHS 158C. Color, abaxial surface — Yellow-green, RHS 143B, with irregular longitudinal stripes colored with a mixture of white, RHS 155A, and yellow-white, nearest to RHS 158C.

Inflorescence: *Monstera* deliciosa typically produces a spathe and spadix inflorescence, but no flowering of the claimed plant has been observed to date.

Flower buds: No flowering has been observed to date.

Flowers: No flowering has been observed to date.

Reproductive organs: No flowering has been observed to date.

Seed and fruit: Seed production has not been observed.

Comparisons with the parent: Plants of the new cultivar 'Sumi1' may be distinguished from the parent, *Monstera deliciosa* 'Thai Constellation' (not patented), by the characteristics described in Table 1.

TABLE 1

| Characteristic | 'Sumi1' | 'Thai Constellation' |
|---|---|---|
| Plant size. | Significantly smaller than 'Thai Constellation' | Significantly larger than 'Sumi1'. |
| Petiole length. | Significantly shorter than 'Thai Constellation'. | Significantly longer than 'Sumi1'. |
| Lamina size. | Significantly smaller than 'Thai Constellation' | Significantly larger than 'Sumi1'. |
| Foliar margins. | Less incised than 'Thai Constellation'. | More heavily incised than 'Sumi1'. |

Comparisons with the most similar commercial variety: Plants of the new cultivar 'Sumi1' may be distinguished from the most similar commercial comparator known to the inventor, *Monstera deliciosa* 'Albo' (not patented), by the characteristics described in Table 2.

TABLE 2

| Characteristic | 'Sumi1' | 'Albo' |
|---|---|---|
| Plant size. | Significantly smaller than 'Albo'. | Significantly larger than 'Sumi1'. |
| Petiole length. | Significantly shorter than 'Albo'. | Significantly longer than 'Sumi1'. |
| Lamina size. | Significantly smaller than 'Albo'. | Significantly larger than 'Sumi1'. |
| Expression of the foliar color patterns; adaxial and abaxial surfaces. | Irregularly flecked and blotched with a mixture of white, pale yellow-white, and pale orange-white. | Irregularly flecked and blotched with cream white; additionally, large portions of the laminar surface are solid cream white. |

That which is claimed is:

1. A new and distinct variety of *Monstera deliciosa* plant named 'Sumi1', substantially as described and illustrated herein.

* * * * *